(12) United States Patent
Maier et al.

(10) Patent No.: US 6,620,598 B2
(45) Date of Patent: Sep. 16, 2003

(54) PROCESS FOR PREPARING O-ACETYL-L SERINE BY FERMENTATION

(75) Inventors: Thomas Maier, Dachau (DE); Tobias Dassler, München (DE); August Böck, Geltendorf (DE)

(73) Assignee: Consortium fur Elektrochemische Industrie GmbH, Munich (DE)

( * ) Notice: Subject to any disclaimer, the term of this patent is extended or adjusted under 35 U.S.C. 154(b) by 11 days.

(21) Appl. No.: 10/077,022

(22) Filed: Feb. 14, 2002

(65) Prior Publication Data

US 2002/0146783 A1 Oct. 10, 2002

(30) Foreign Application Priority Data

Feb. 15, 2001 (DE) .......................... 101 07 002

(51) Int. Cl.⁷ ............................ C12P 13/04; C12P 13/06
(52) U.S. Cl. ........................ 435/106; 435/116; 435/232; 435/252.3; 435/252.33
(58) Field of Search ................. 435/106, 232, 435/252.3, 252.33, 116

(56) References Cited

U.S. PATENT DOCUMENTS 5,972,663 A 10/1999 Winterhalter et al.
6,218,168 B1 * 4/2001 Leinfelder et al. ....... 435/252.3

FOREIGN PATENT DOCUMENTS

| EP | 0885962 | 12/1998 |
| EP | 0994 190 | 4/2000 |
| WO | 97 15673 | 5/1997 |
| WO | 0044923 | 8/2000 |

OTHER PUBLICATIONS

Knedich N. M. et al., (1966) Journal of Biological Chemistry, The American Society of Biological Chemists Inc.,, US, vol. 241, No. 21, pp. 4955–4965.

Tai et al., Biochemistry, vol. 34, No. 38, 1995, pp. 12311–12322.

Patents Abstracts of Japan. JP 11299491A Nov. 1999.

Patents Abstracts of Japan. JP 9009982 A Jan. 1997.

Chemical Abstracts AN 133: 174344 Mol. Microbiol. (2000/36(5) 1101–1112.

DaBler et al., 2000 Molecular Microbiology, 36 (5), pp. 1101–1112.

Nakamoris et al., 1998, Appl. and Environmental Microbiology, 64, pp 1607–1611.

Tagakitt. et al., 1999, FEBS Lett. 452, pp. 323–327.

* cited by examiner

Primary Examiner—Herbert J. Lilling
(74) Attorney, Agent, or Firm—Collard & Roe, P.C.

(57) ABSTRACT

A process is provided for the fermentative preparation of O-acetyl-L-serine. A microorganism strain, which is derived from a wild type and which exhibits an increased endogenous formation of O-acetyl-L-serine and an increased efflux of O-acetyl-L-serine as compared with the wild type, is cultured in a fermentation medium. A pH in the range from 5.1 to 6.5 is set in the fermentation medium.

21 Claims, 1 Drawing Sheet

PROCESS FOR PREPARING O-ACETYL-L SERINE BY FERMENTATION

BACKGROUND OF THE INVENTION

1. Field of the Invention

The invention relates to a process for preparing O-acetyl-L-serine by means of fermentation.

2. The Prior Art

Fermentative processes for preparing amino acids are nowadays commonplace. These processes are, in particular, methods for preparing representatives of the twenty proteinogenic amino acids which are highly relevant from the economic point of view, such as L-glutamic acid, L-lysine and L-threonine. However, there is an increasing number of reports of processes for preparing proteinogenic amino acids which command smaller markets in the range of from 1000 to 10,000 tons per year, such as L-phenylalamine and L-cysteine.

By contrast, scarcely any corresponding methods are known for preparing biosynthetic precursors of the twenty proteinogenic amino acids. However, it is precisely these precursors which can represent interesting products since they frequently possess chiral centers and can serve as building blocks for synthesizing pharmaceutical active compounds. For example, patent application WO 00/44923 describes the preparation of shikimic acid, which is an intermediate in the biosynthesis of aromatic amino acids. Another example is that of application EP 0994190 A2, which reports the use of fermentation to produce L-homoserine, which is a precursor of L-methionine.

O-Acetyl-L-serine is a biosynthetic precursor of L-cysteine. It is an amino acid in its own right and is formed in bacterial and plant metabolism by L-serine being acetylated at the hydroxyl function. This reaction is catalyzed by the enzyme serine O-acetyltransferase [EC 2.3.1.30], which is encoded by the cysE gene. In the cell, O-acetylserine is subjected to further reaction to form L-cysteine. In this reaction, the acetate function is replaced with a thiol function.

Difficulties with preparing o-acetyl-L-serine by fermentation result from the fact that the substance is very labile and isomerizes to N-acetyl-L-serine at pH values above 4.0. At a pH of 7.6, the rate of the reaction is $1\% \times min^{-1}$ (Tai et al., 1995, Biochemistry 34: 12311–12322). This means that no significant quantities of O-acetylserine can be detected under these conditions after a fermentation process which is usually conducted for at least one-and-a-half days. The isomerization reaction is irreversible and its rate increases still further as the pH increases. Because its amino function is blocked, N-acetyl-L-serine can no longer be used for peptide syntheses, in contrast to O-acetyl-L-serine.

Another difficulty is that the level of O-acetyl-L-serine in the cell is very low and is subject to powerful regulation. On the one hand, serine acetyltransferase is inhibited allosterically by L-cysteine, and no synthesis of O-acetyl-L-serine is consequently possible in the presence of $\mu M$ concentrations of L-cysteine. On the other hand, the isomerization product N-acetyl-L-serine acts as an inducer of the sulfur regulon and thereby leads to the rapid reaction of O-acetyl-L-serine with sulfide to form L-cysteine.

Dassler et al. (2000, Mol. Microbiol. 36: 1101–1112) have reported that cells which overproduce the membrane protein YdeD (=Orf299) secrete L-cysteine, 2-methylthiazolidine-2,4-dicarboxylic acid and also O-acetyl-L-serine into the culture medium. However, it was possible to detect the O-acetyl-L-serine only in very small quantities, of 0.12 g/l, and then only in shaking flask experiments. On the other hand, only N-acetyl-L-serine was obtained in fermentation experiments which enable higher yields to be obtained as a result of improving the nutrient supply. The possibility has been discussed that O-acetyl-L-serine is sufficiently stable only at pH values of 4–5. However, this pH range is not suitable for a fermentative preparation due to the poor growth of neutrophilic bacteria such as *Escherichia coli*.

The fermentative preparation of N-acetyl-L-serine at pH 7.0 using Orf299 has also been described in patent application EP 0885962 A1. In this case, the orf299 gene (designated by SEQ.ID.NO:3 in the application) was combined with suitable cysE alleles. These alleles encoded serine acetyltransferases which were subject to less feedback inhibition by L-cysteine. This resulted in an increased production of O-acetyl-L-serine being achieved in the cell and ultimately in the accumulation of N-acetyl-L-serine due to the rapid isomerization.

Using cysE alleles which are subject to less feedback inhibition on their own, as described in application WO 97/15673, does not lead to the accumulation of O-acetyl-L-serine, either. While an increased formation of O-acetyl-serine is achieved intracellularly when this approach is used, only L-cysteine was detected extracellularly and was consequently within reach as a product.

A further serious difficulty when producing O-acetyl-L-serine is the fact, reported by Dassler et al. (2000, Mol. Microbiol. 36: 1101–1112), that overproduction of Orf299 leads to severe impairment of bacterial growth. This is due to the absence of induction of the sulfur regulon because of the intracellular deficiency of the inducer N-acetyl-L-serine.

SUMMARY OF THE INVENTION

It is an object of the invention to provide a fermentative process which provides high yields of O-acetyl-L-serine despite the instability of O-acetyl-L-serine and the negative physiological consequences of efficiently exporting O-acetyl-L-serine from the cell.

This object is achieved by culturing, in a fermentation medium, a microorganism strain which is derived from a wild type and in which the endogenous formation of O-acetyl-L-serine and the efflux of O-acetyl-L-serine are increased as compared with the wild type, wherein the pH in the fermentation medium is adjusted to be within the range from 5.1 to 6.5.

It has unexpectedly and surprisingly been found:

that a microorganism strain which is characterized as described above secretes O-acetyl-L-serine in large quantities, that O-acetyl-L-serine is sufficiently stable in the fermentation medium at pH values of from 5.1 to 6.5, and that, at the same time, the abovementioned physiological problems of an o-acetyl-L-serine-secreting cell can to a large extent be remedied by supplying O-acetyl-L-serine in increased amounts using feedback-resistant cysE alleles.

The pH of the fermentation medium during fermentation is preferably in the pH range from 5.5 to 6.5; and a pH of from 5.5 to 6.0 is particularly preferred.

Microorganism strains which can be used in the process according to the invention are distinguished by the fact that they exhibit an increased endogenous formation of O-acetyl-L-serine, and exhibit an increased efflux of O-acetyl-L-serine.

Strains of this nature are known in the state of the art. An increased endogenous formation of O-acetyl-L-serine can be achieved by introducing modified cysE alleles, as described, for example, in WO 97/15673 (hereby incorporated by reference) or Nakamori S. et al., 1998, Appl. Env. Microbiol. 64: 1607–1611 (hereby incorporated by reference) or Takagi H. et al., 1999, FEBS Lett. 452: 323–327 into a microorganism strain.

These cysE alleles encode serine O-acetyltransferases which are subject to a diminished feedback inhibition by cysteine. As a result, the formation of O-acetyl-L-serine is to a large extent uncoupled from the cysteine level in the cell.

An increased O-acetyl-L-serine efflux can be achieved by increasing the expression of an efflux gene whose gene product brings about the export of O-acetyl-L-serine.

The ydeD gene, which has been described by Dassler et al. (2000, Mol. Microbiol. 36: 1101–1112) and in EP 0885962 A1 (corresponds to the US application with the Ser. No. 09/097,759 (hereby incorporated by reference)) is a particularly preferred efflux gene of this nature.

The modified cysE alleles and/or the efflux gene may be present in the strain employed in single copies or else in increased copy number. They may be encoded chromosomally or be located on self-replicating elements, such as plasmids.

The expression of the genes can be increased, for example, by using suitable promoter systems which are known to a person skilled in the art.

In a preferred embodiment of the present invention, use is made of a microorganism which harbors a cysE allele and/or a ydeD gene, having a native promoter or the gapDH promoter, on a plasmid having a medium-range copy number. An example of such a construct is pACYC184-cysEX-GAPDH-ORF306, which is described in detail in EP 0885962 A1.

In principle, all microorganism strains which are accessible to genetic methods and which can be readily cultured in a fermentation process are suitable for preparing strains of this nature. Preference is given to using bacteria of the Enterobacteriaceae family. Particular preference is given to using organisms of the species *Escherichia coli*. The preparation of these strains is described in the abovementioned documents and is not part of the present invention.

Strains which are suitable for the process according to the invention are also suitable—as described in EP 0885962 A1 (corresponds to the U.S. Patent application having the Ser. No. 09/097,759 (herewith incorporated by reference))—for preparing cysteine and cysteine derivatives. However, in this case, an adequate supply of an inorganic sulfur source, such as sulfate or thiosulfate, is required in order to obtain optimum quantities of L-cysteine or one of its derivatives.

However, in the process according to the invention, no sulfur source is metered in during the fermentation since the further conversion of O-acetyl-L-serine into cysteine is unwanted. It is only necessary to ensure that an adequate quantity of a sulfur or S source (e.g. sulfate or thiosulfate) is present in the medium so as to cover the requirement of the cellular protein synthesis for cysteine. The adequate quantity in the nutrient medium is preferably from 5 to 50 mM sulfur.

The process according to the invention for preparing O-acetyl-L-serine using a microorganism strain is performed in a fermenter in a manner which is known per se but while setting unusually low pH values during the fermentation.

The microorganism strain is grown in the fermenter as a continuous culture, as a batch culture or, preferably, as a fed-batch culture. Particularly preferably, a carbon or C source is metered in continuously during the fermentation.

Preference is given to using sugar, sugar alcohols or organic acids as the C source. The C sources which are particularly preferably used in the process according to the invention are glucose, lactose or glycerol.

The C source is preferably metered in, in a form which ensures that the content in the fermenter during the fermentation is maintained in a range of 0.1–50 g/l. A range of 0.5–10 g/l is particularly preferred.

The nitrogen or N source which is preferably used in the process according to the invention is ammonia, ammonium salts or protein hydrolyzates. When ammonia is used as the correcting agent for maintaining a constant pH, this N source is then regularly fed in during the fermentation.

Other medium additives which may be added are salts of the elements phosphorus, chlorine, sodium, magnesium, nitrogen, potassium, calcium and iron. Trace amounts (i.e. in $\mu$M concentrations), of salts of the elements molybdenum, boron, cobalt, manganese, zinc and nickel, may also be added.

It is furthermore possible to add organic acids, or salts of these acids, (e.g. acetate or citrate), amino acids (e.g. isoleucine) and vitamins (e.g. B1, B6) to the medium.

Examples of complex nutrient sources which may be used are yeast extract, corn steep liquor, soybean meal and malt extract.

The incubation temperature is 15–45° C. A temperature of between 30 and 37° C. is preferred.

The fermentation is preferably carried out under aerobic growth conditions. Oxygen is fed into the fermenter using compressed air or pure oxygen.

Microorganisms which are fermented in accordance with the process of the present invention which has been described, secrete O-acetyl-L-serine into the culture medium with a high degree of efficiency over a fermentation period of from 1 to 3 days.

BRIEF DESCRIPTION OF THE DRAWINGS

Other objects and features of the present invention will become apparent from the following detailed description considered in connection with the accompanying drawing. It is to be understood, however, that the drawing is designed as an illustration only and not as a definition of the limits of the invention.

In the drawing.

DETAILED DESCRIPTION OF THE PREFERRED EMBODIMENT

Figure 1:
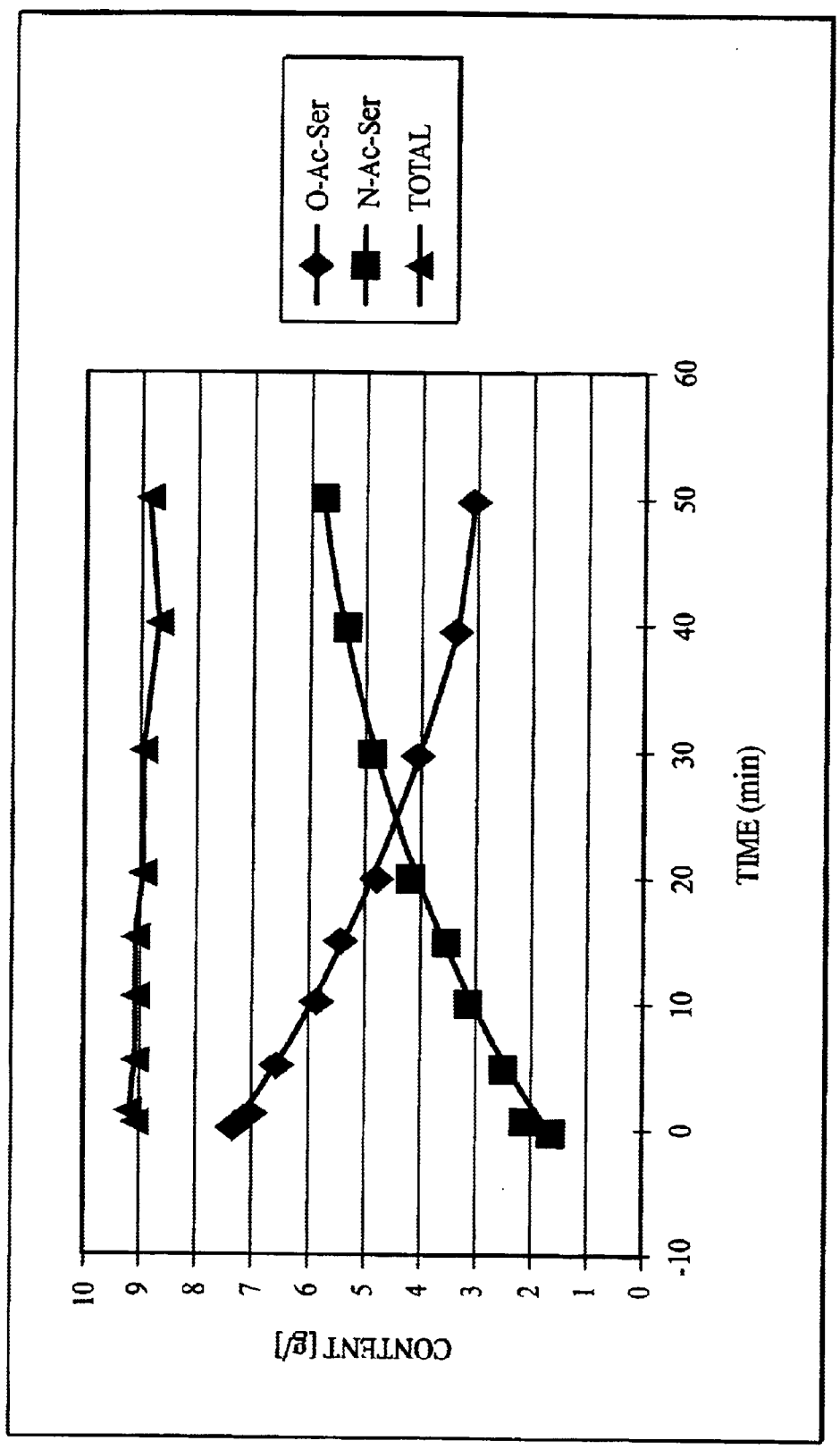
FIG. 1 shows the total content of acetyl-serine versus time.

The following examples serve to further clarify the invention. The bacterial strain *Escherichia coli* W3110/pACYC184-cysEX-GAPDH-ORF306, which was used for carrying out the examples, was deposited, in accordance with the Budapest Treaty, in the DSMZ (Deutsche Sammlung für Mikrooganismen und Zellkulturen [German Collection of Microorganisms and Cell Cultures] GmbH, D-38142 Brunswick) under the number DSM 13495.

EXAMPLE 1

Isomerisation of O-acetyl-L-serine to N-Acetyl-L-serine

In order to gain a more accurate impression of the isomerization reaction under conditions approximating to those of fermentation, 0.9 g of O-acetyl-L-serine was introduced into 100 ml of fermentation medium (see Example 3). The pH was then adjusted to 7.0 using 25% ammonia and samples were withdrawn at various times while maintaining a reaction temperature of 32° C. These samples were analyzed by reversed phase HPLC performed on a LUNA 5μ C18(2) column, (Phenomenex, Aschaffenburg, Germany). Dilute phosphoric acid (0.1 ml of conc. phosphoric acid/l) was used as the eluent, at a flow rate of 0.5 ml/min. The results are shown in FIG. 1.

EXAMPLE 2

Preliminary Culture of the Production Strain

As the preliminary culture for the fermentation, 20 ml of LB medium (10 g of tryptone/l, 5 g of yeast extract/l, 10 g of NaCl/l), which additionally contained 15 mg of tetracycline/l, were inoculated with the strain W3110/pACYC184-cysEX-GAPDH-ORF306 (described in EP 0885962 Al, corresponds to the U.S. Patent application having the Ser. No. 09/097759 (hereby incorporated by reference)) and incubated at 30° C. and 150 rpm in a shaker incubator. After seven hours, the whole mixture was transferred to 100 ml of SM1 medium (12 g of $K_2HPO_4$/l; 3 g of $KH_2PO_4$/l; 5 g of $(NH_2)_2SO_4$/l; 0.3 g of $MgSO_4 \times 7H_2O$/l; 0.015 g of $CaCl_2 \times 2H_2O$/l; 0.002 g of $FeSO_4 \times 7H_2O$/l; 1 g of $Na_3$citrate$\times 2H_2O$/l; 0.1 g of NaCl/l; 1 ml of trace element solution/l, with this solution consisting of 0.15 g of $Na_2MoO_4 \times 2H_2O$; 2.5 g of $Na_3BO_3$/l; 0.7 g of $CoCl_2 \times 6H_2O$/l; 0.25 g of $CuSO_4 \times 5H_2O$/l; 1.6 g of $MnCl_2 \times 4H_2O$/l; 0.3 g of $ZnSO_4 \times 7H_2O$/l) which was supplemented with 5 g of glucose/l; 0.5 mg of vitamin $B_1$/l and 15 mg of tetracycline/l. The subsequent incubation took place at 30° C. for 17 hours and at 150 rpm.

EXAMPLE 3

Preparation of o-acetyl-L-serine by Fermentation

The fermenter employed was a Biostat M appliance, which was supplied by Braun Biotech (Melsungen, Germany) and which has a maximum culture volume of 2 l. The fermenter, containing 900 ml of fermentation medium (15 g of glucose/l; 10 g of tryptone/l; 5 g of yeast extract/l; 5 g of $(NH_4)_2SO_4$/l; 1.5 g of $KH_2PO_4$/l; 0.5 g of NaCl/l; 0.3 g of $MgSO_4 \times 7H_2O$/l; 0.015 g of $CaCl_2 \times 2H_2O$/l; 0.075 g of $FeSO_4 \times 7H_2O$/l; 1 g of $Na_2$citrate$\times 2H_2O$/l and 1 ml of trace element solution, see above,/l, 5 mg of vitamin B1/l and 15 mg of tetracycline/l, adjusted to pH 6.0 with 25% ammonia) was inoculated with the preliminary culture described in Example 2) optical density at 600 nm of approx. 3). During the fermentation, the temperature was set to 32° C. and the pH was kept constant at a value of 6.0 by metering in 25% ammonia. The culture was gassed with sterilized compressed air at the rate of 1.5 vol/vol/min and stirred using a stirrer speed of 200 rpm. After the oxygen saturation had fallen to value of 50%, the rotational speed of the stirrer was increased, by way of a controlling device, to a value of 1200 rpm in order to maintain 50% oxygen saturation (determined using a $pO_2$ probe calibrated to 100% saturation at 900 rpm). A 56% solution of glucose was metered in as soon as the glucose content in the fermenter, which was originally 15 g/l, had fallen to approx. 5–10 g/l. The feeding-in took place at a flow rate of 6–12 ml/h, with the glucose concentration in the fermenter being maintained constant at between 0.5 and 10 g/l. The glucose was determined using the glucose analyzer supplied by YSI (Yellow Springs, Ohio, USA). The fermentation lasted for 28 hours. After this time, samples were removed and the cells were separated off from the culture medium by centrifugation. The resulting culture supernatants were analyzed by reversed phase HPLC as described in Example 1. Table 1 shows the content of the main metabolic products which were achieved in the culture supernatant:

TABLE 1

| Metabolite | Content [g/l] |
| --- | --- |
| O-acetyl-L-serine | 9.0 |
| N-acetyl-L-serine | 4.2 |
| 2-methylthiazolidine-2,4-dicarboxylic acid | 1.9 |

Similar values were obtained in the range from pH 6.5 to pH 5.5.

Accordingly, while only several embodiments of the present invention have been shown and described, it is obvious that many changes and modifications may be made thereunto without departing from the spirit and scope of the invention.

What is claimed is:

1. A process for a fermentative preparation of O-acetyl-L-serine, comprising
   culturing a microorganism strain, which is derived from a wild type and which exhibits an increased endogenous formation of O-acetyl-L-serine and an increased efflux of O-acetyl-L-serine as compared with the wild type, in a fermentation medium; and
   setting a pH in the range from 5.1 to 6.5 in the fermentation medium.

2. The process as claimed in claim 1,
   wherein the pH of the fermentation medium during the fermentative preparation is in the pH range from 5.5 to 6.5.

3. The process as claimed in claim 2,
   wherein the pH of the fermentation medium during the fermentative preparation is in the pH range from 5.5 to 6.0.

4. The process as claimed in claim 1,
   wherein the increased endogenous formation of O-acetyl-L-serine, as compared with the wild type, is achieved using a cysE allele which encodes a serine acetyltransferase which is subject to less feedback inhibition.

5. The process as claimed in claim 1,
   wherein the increased efflux of O-acetyl-L-serine, as compared with the wild type, is achieved using a ydeD gene.

6. The process as claimed in claim 1,
   wherein the microorganism strain is *Escherichia coli*.

7. The process as claimed in claim 1,
   wherein the microorganism strain is grown in a fermenter selected from the group consisting of a continuous culture, a batch culture, and a fed-batch culture.

8. The process as claimed in claim 1,
   wherein the nutrient medium contains an S source at a concentration of 5–50 mM sulfur.

9. The process as claimed in claim 1,
   wherein a C source is metered in continuously during the fermentative preparation.

10. The process as claimed in claim 9,
    wherein the C source is selected from the group consisting of sugar, sugar alcohols and organic acids.

11. The process as claimed in claim 9,
    wherein the C source is selected from the group consisting of glucose, lactose and glycerol.

12. The process as claimed in claim 9, wherein the C source is metered in such that it is present in a range of 0.1–50 g/l during the fermentation.

13. The process as claimed in claim 1, wherein an N source is added and is selected from the group consisting of ammonia, ammonium salts and protein hydrolyzates.

14. The process as claimed in claim 1, wherein salts of elements selected from the group consisting of phosphorus, chlorine, sodium, magnesium, nitrogen, potassium, calcium and iron and, in traces (i.e. in $\mu$M concentrations), salts of elements selected from the group consisting of molybdenum, boron, cobalt, manganese, zinc and nickel, are added to the fermentation medium.

15. The process as claimed in claim 1, wherein a substance selected from the group consisting of organic acids, acetate, citrate, amino acids, isoleucine, vitamins, B1, and B6 is added to the fermentation medium.

16. The process as claimed in claim 1, wherein a substance selected from the group consisting of yeast extract, corn steep liquor, soybean meal, and malt extract is added to the fermentation medium.

17. The process as claimed in claim 1, wherein an incubation temperature of between 15 and 45° C. is used.

18. The process as claimed in claim 17, wherein the incubation temperature is between 30 and 37° C.

19. The process as claimed in claim 1, wherein the process is carried out under aerobic growth conditions.

20. The process as claimed in claim 19, wherein the aerobic growth conditions are brought about by introducing oxygen into the fermenter by means selected from the group consisting of compressed air, and pure oxygen.

21. The process as claimed in claim 1, wherein a fermentation time of from 1 to 3 days is selected.

* * * * *